United States Patent [19]
Bayers

[11] 4,134,161
[45] Jan. 16, 1979

[54] ADJUSTABLE INTRAOCULAR LENS

[76] Inventor: Jon H. Bayers, 1042 Panadero Ct., Clayton, Calif. 94517

[21] Appl. No.: 893,948

[22] Filed: Apr. 6, 1978

Related U.S. Application Data

[63] Continuation-in-part of Ser. No. 778,123, Mar. 16, 1977.

[51] Int. Cl.² .......................... A61F 1/16; A61F 1/24
[52] U.S. Cl. ................................................. 3/13
[58] Field of Search ........................................ 3/1, 13

[56] References Cited

U.S. PATENT DOCUMENTS 2,834,023  5/1958  Lieb ............................................ 3/13

OTHER PUBLICATIONS

"Experience with Twelve Cases of Intra–Ocular Anterior Chamber Implants for Aphakia" by J. Boberg-Ans, British Journal of Ophthalmology, vol. 45, No. 1, Jan. 1961, pp. 37–43.

The Mark VI, Mark VII and Mark VIII Choyce Anterior Chamber Implants, Proceedings of The Royal Society of Medicine, vol. 58, Sep. 1965, pp. 729–731.

Primary Examiner—Ronald L. Frinks
Attorney, Agent, or Firm—Bielen and Peterson

[57] ABSTRACT

An intraocular lens utilizing an optical lens portion adapted to position over the pupil along the optical axis. The lens includes a first member extending away from the lens portion to the periphery of the iris of the eye and being fixed to the lens portion. A second adjustable member includes a projecting element and a wedging piece which are forced toward one another, causing fixation of the lens portion.

6 Claims, 13 Drawing Figures

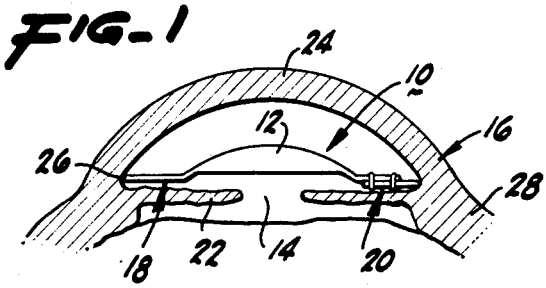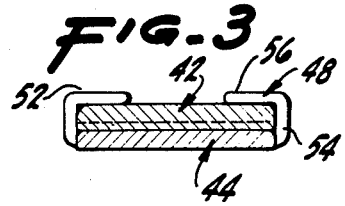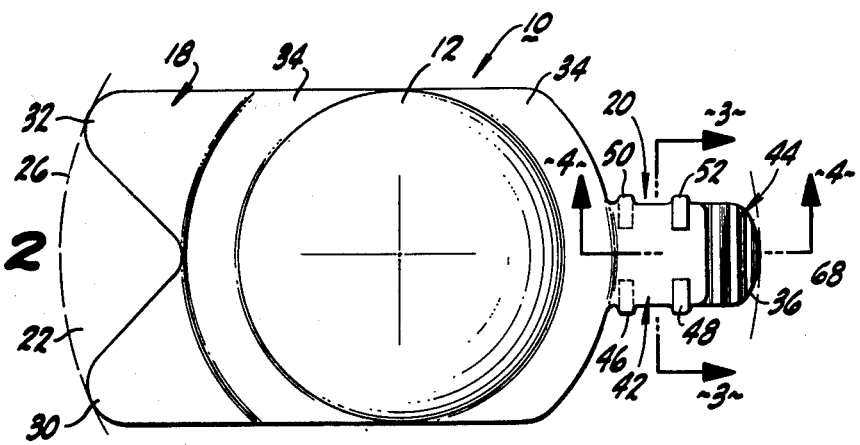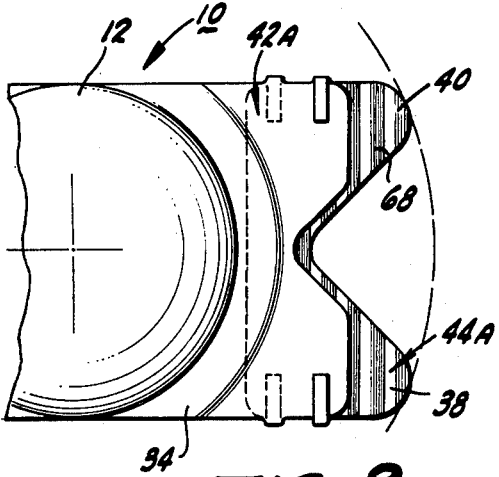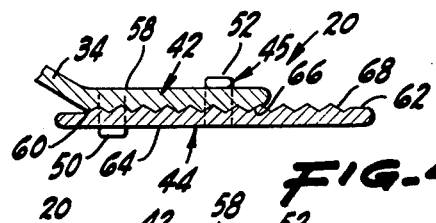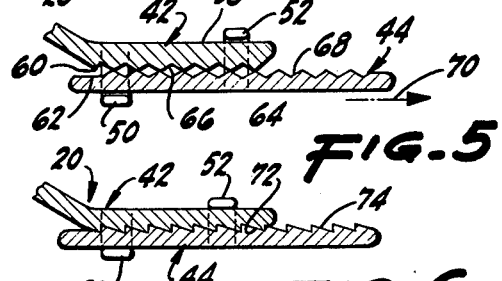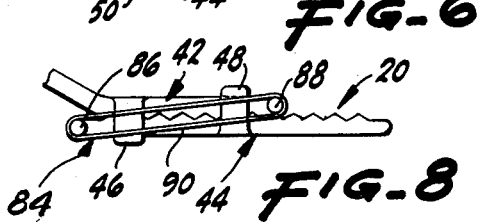

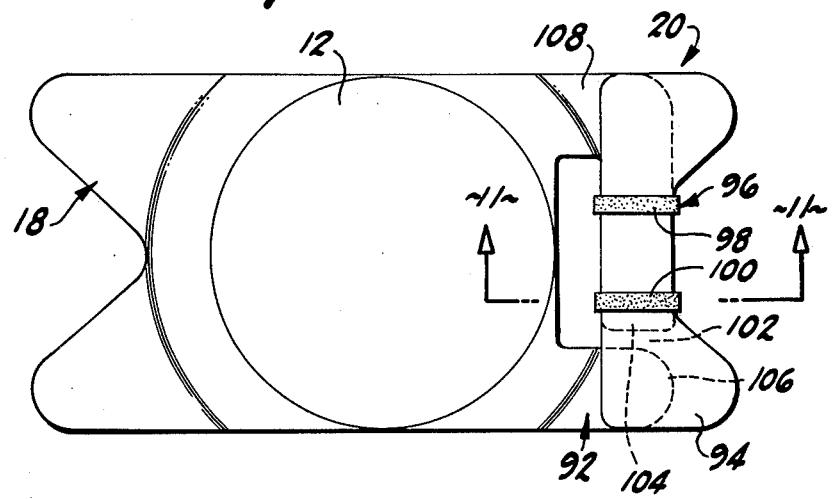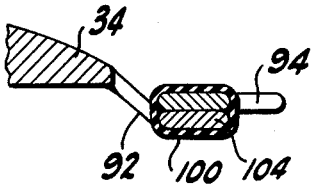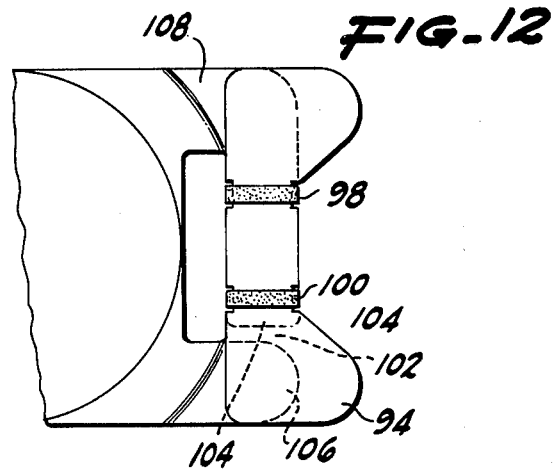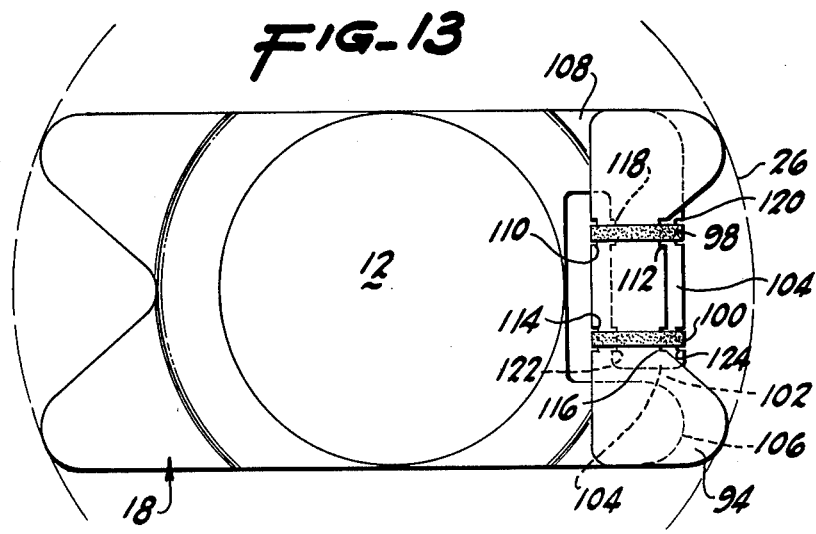

ADJUSTABLE INTRAOCULAR LENS

CROSS REFERENCES TO RELATED APPLICATIONS

The present application is a Continuation-in-part of my prior application, Ser. No. 778,123, filed 16 Mar. 1977.

BACKGROUND OF THE INVENTION

The present invention relates to intraocular lens systems or pseudophakos generally implanted after removal of the natural lens of an eye as a result of a cataract condition.

The problem of correcting impaired vision of an eye after cataract surgery has been tackled in various ways. The prior methods for remedying the blurred vision condition has included the use of eyeglasses which has the undesirable side effect of reducing peripheral vision and magnifying the visual image obtained by the eye being corrected. Cataract removal and correction of vision by eyeglasses produces double vision. Contact lenses offer a better solution, although not a perfect one, since magnification still occurs. Moreover, contact lenses are relatively difficult to wear by the majority of cataract post-operative patients.

Intraocular lens implantation solves the majority of the optical problems associated with natural lens removal. New problems arise with the insertion of pseudophakos, for example, the fixation, support, relocation, and sterilization of such artificial lens systems.

Most of the prior intraocular lenses have been positioned in the anterior chamber of the eye. The Ridley, Epstein, Binkhorst, and Copeland, lenses employ a variety of clips, loops, and stabilizers to fasten the lens to the iris portion of the eye. Reference is made to U.S. Pat. No. 3,906,551 issued to Otter and U.S. Pat. No. 3,922,728 to Krasnov as representative of artificial lens designs. Insertion of these lenses requires great surgical skill.

Other lenses have been placed in the posterior chamber of the eye, with less success because of the difficulty involved with such fixation and positioning. Ophthalmologic surgeons have favored anterior chamber intraocular lens placement because of the relative remoteness of the posterior chamber and of the additional skill needed to successfully perform posterior chamber implantations. In this regard, the U.S. Pat. No. 3,711,870 to Deitrick and the U.S. Pat. No. 3,991,426 to Flom describe examples of posterior chamber lens devices.

An early development by Strampelli, in 1953, used the idea of placing an intraocular lens over the iris and into a wedging configuration between the periphery of the iris and the connecting sclera commonly referred to as the anterior chamber angle. This lens made extensive contact with the trabeculum and corneal endothelium, causing damage to both structures.

A later variation of the Strampelli lens was the Choyce family of lenses which reduced the radius thickness of the Strampelli lens. Less tissue reactive materials were used for the entire lens, also. However, the Choyce lenses have a tendency to dislocate inferiorly, which requires reentry into the eye for relocation of the lens or insertion of a new lens. To avoid a misfitting of the lens, the proper sized lens must be initially inserted. Measurement across the iris, from opposite points of the angle, vary from about 12 to 14 millimeters. Exact dimensioning across the anterior chamber of an eye cannot be determined accurately without entering the eye. Incision of the eye invariably releases aqueous humor causing the eye to change its exterior shape; becoming more oblate. Such deformation renders actual measurement unlikely, if not impossible. The method now used to measure the Choyce lens adds a fixed dimension to the horizontal exterior white-to-white length. The results are not completely accurate.

If an accurate measurement is to be obtained, the eye surgeon must have the proper sized lens immediately prepared for implantation. This procedure entails maintaining a complete line of intraocular lenses according to length and refractive power.

The current procedure for insertion of the Choyce lens requires filling the eye anterior chamber with balanced salt solution after insertion of a lens and later nudging or tapping the sclera perpendicular to the axis of the lens. If the lens is stable, the fit is proper, if the lens moves it is too short. The latter instance requires re-opening the chamber and inserting a longer lens. Post-operative patients are examined and made to blink to see if the lens is stable, again if the lens moves a new longer lens is required for re-insertion.

SUMMARY OF THE INVENTION

In accordance with the present invention a novel adjustable intraocular lens is provided. An optical zone or lens portion adopted for positioning over the pupil includes a first member, fixed to the lens portion, which extends away from the same to the periphery of the iris. A second adjustable member also connects to the lens portion. Adjustments of the extension of the second member away from the lens portion, wedges the intraocular lens into place beneath the cornea of an eye. The wedging takes place at an angle or scleral spur at the periphery of the iris in the anterior chamber.

The first member may include two edge portions spaced from one another about the outer periphery of the iris. This provision would provide a roughly tripod support for the optical zone. Likewise, the second member may include two spaced edge portions which permits the insurance of at least a tripod support if one of the edge portions of the first and second members does not wedge properly.

The second adjustable member has several possible configurations, the importance being that the second adjustable member expands or contracts to effect the wedging of the intraocular lens. The second adjustable member may include a first tongue or projection connected to the lens portion and a second tongue or projection being adjacent the first tongue. Means for positioning the first tongue in relation to the second tongue effectively wedges the intraocular lens into a fixed position by dint of the contact of the edges of the first and second member at the angle or scleral spur portion of the eye.

The positioning means of the second member may take many forms and may include, as an element of one of these forms, clamping means for releasably holding the first tongue against the second tongue. The first and second tongues may have serrations on opposing surfaces that mate and lock the respective position of the tongues at a plurality of positions. Thus, the extension of the second member may be predetermined by "clicking" the first and second tongues into place with respect to one another. The clamping means would hold and guide the mated serrated surfaces in position with respect to one another, yet allow the seeking of a new position by permitting the separation of the tongues during relative movement therebetween. The serrations may be designed to allow back-and-forth or one-way movement of the second tongue or the relative movement between the tongues.

In addition, the present invention may include a pair of ears on each of the tongues for receiving a positioning force applied thereto. For instance, the ears may shorten or lengthen the second adjustable member by inserting elongated surgical tools through the limbus or cornea. This feature would permit readjustment of the fit of the intraocular lens for various reasons; for example, reappearance of aqueous humor post-operative to cataract removal, changing of the shape of the eye.

The avoidance of intraocular surgical manipulations would be realized with means for continually forcing the second tongue away from the first tongue. Such means may take the form of an elastic member contacting a pair of studs on extensions each radiating from the first and second tongues. The force of the elastic member urges separation of the tongues and thus maintains the wedging action of the intraocular lens.

As may be surmised, a new and useful intraocular lens has been provided for correcting the vision of eyes, especially after cataract removal.

It is, therefore, an object of the present invention to provide an intraocular lens useable after extracapsular or intracapsular cataract removal.

It is another object of the present invention to provide an intraocular lens easily insertable and having an adjustable fit to accomodate variations in eye sizes and shapes.

It is yet another object of the present invention to provide an intraocular lens having adjustability characteristics before and after insertion within an eye.

It is another object of the present invention to provide an intraocular lens which obviates the need for loop, clips, and other appendages thereto, yet fixes within the eye quickly and safely without premeasurement of the external or internal dimensions of the eye.

It is yet another object of the present invention to eliminate or greatly reduce the inventory of various sized intraocular lenses for use during cataract surgery.

It is another object of the present invention to provide an intraocular lens whose fit is automatically adjusted within the eye.

The invention possesses other objects and advantages especially as concerns particular features and characteristics thereof which will become apparent as the specification continues.

Various aspects of the present invention will evolve from the following detailed description of the preferred embodiments thereof which should be taken in conjunction with the accompanying drawings.

BRIEF DESCRIPTION OF THE DRAWINGS

FIG. 1 is a sectional view of the intraocular lens within the eye.

FIG. 2 is a top plan view of the invention.

FIG. 3 is a view taken along line 3—3 of FIG. 2.

FIG. 4 is a view taken along line 4—4 of FIG. 2.

FIG. 5 is a sectional view showing the relative movements of the tongues of FIG. 4.

FIG. 6 is a sectional view of a portion of the invention showing a variation of the design of the interlocking surfaces of the tongues.

FIG. 7 is a sectional view of a portion of the invention showing the provision of ears.

FIG. 8 is a sectional view of a portion of the invention showing continual forcing means.

FIG. 9 is a partially broken plan view of the invention showing two spaced edge portions of the second adjustable member.

FIG. 10 is a top plan view of another embodiment of the invention.

FIG. 11 is a view taken along line 11—11 of FIG. 10.

FIG. 12 is a broken top plan view of yet another embodiment of the invention.

FIG. 13 is a top plan view of the FIG. 12 embodiment in place within eye.

DESCRIPTION OF THE PREFERRED EMBODIMENTS

The invention as a whole depicted in the Figures is denoted by reference character 10 and includes, as one of its elements, a lens portion 12 lying over the pupil 14 of an eye 16. The lens portion 12 may be constructed of any biologically inert, transparent material, such as methylmethacrylate quartz, ophthalmic glass, and other polymerized materials known in the art.

Fixed to lens portion 12 is a first member 18 and a second adjustable member 20 which may be formed of the same material as lens portion 12 or of different material from lens portion 12. Of course, first and second adjustable members 18 and 20 must be biologically inert and non-absorbtive in relation to living tissue. The first and second members 18 and 20 extend from lens portion 12 to the periphery of iris 22 of eye 16 by known surgical methods and wedges into a fixed position within eye 16 at the vicinity of angle 26 (the general meeting place of cornea 24, iris 22, and sclera 28), FIG. 1. The intraocular lens 10 may wedge into the angle 26 at the scleral spur (not shown). Lens portion 12 may take the form of a plano-convex optical configuration, but may be of any lens shape and power known in the art of vision correction. Typically, lens portion 12 may possess between 17 and 21 diopters of power.

FIG. 2 most clearly shows an embodiment of the intraocular lens 10 where first member 18 includes edge portions 30 and 32 spaced from each other along angle 26. The lens portion 12 first and second member 18 and 20 transition necessitates sloped portion 34. Second adjustable member 20 may embrace a single edge portion 36, FIG. 2, or two spaced edge portions 38 and 40, FIG. 9. The lens 10 embodiment shown in FIG. 2 offers tripod support, while the embodiment of lens 10 depicted in FIG. 9 provides quadrapod support, and at least tripod support if one edge portion of either first or second member 18, 20 does not contact the vicinity of angle 26.

The second adjustable member 20 may embrace a number of embodiments each designed to fill a particular medical need. For instance, FIGS. 1–5 show a first tongue 42 connected to lens portion 12 via sloped portion 34. A second tongue 44 lies adjacent the first tongue 42 in a slidable relationship. Means for positioning the tongues 42 and 44 in relation to one another also contributes to the adjustability of the second member 20. Clamping means 45 comprising clamps 46, 48, 50, and 52 releasably holds tongues 42 and 44 against one another, FIGS. 1–8. The clamps 48 and 52 of FIG. 3 illustrates an embodiment of the clamps. Clamp 48, as exemplar of the remaining clamps 46, 50, and 52, has a first arm 54 and an arm 56; arms 54 and 56 are angularly oriented with respect to one another and integrally formed. Arm 54 of clamp 48 fixes to second tongue 44 by gluing, sonic welding, or molding and the like. Second arm 56 presses tightly upon the surface 58 of first tongue 42, thus pressing tongue 42 into frictional engagement of tongue 44. The second arm 54 of clamp 48 must be able to releasably hold the first tongue 42 to second tongue 44 to permit a degree of sliding therebetween. The net result of the sliding between tongues 42 and 44 is the extension or retraction of second adjustable member 20 from, or to, lens portion 12. Clamps 46, 48, 50, and 52 also guide the movement of tongues 42 and 44.

Serrations 66 and 68 may be added to surfaces 60 and 62 of tongues 42 and 44, to provide a plurality of positions or stops therebetween. Clamps 50 and 52 bear on surface 64 of tongue 44 to aid in mating the tongues to the stops provided by serrations 66 and 68. Clamps 46, 48, 50, and 52 are constructed of resilient material such as nylon, methylmethacrylate and like biologically neutral compounds. With reference to FIG. 5, a positioning force denoted by arrow 70 will force the clamps arms contacting surfaces 58 and 64, outwardly from the serrations 66 and 68. This occurs when the serrations 66 and 68 move relative to each other from the mated position (apex to recess) to an unmated position (apex to apex). Clamp 46, 48, 50, and 52 maintain pressure between surfaces 60 and 62 of tongues 42 and 44, to again force mating of the serrations 66 and 68 at any of the plurality of positions. First and second tongues 42A and 44A may also include serrations 66 and 68, FIG. 9.

FIG. 6 shows serrations 72 and 74 which biases the movement of tongue 44 into the extended position, toward the right. This feature would prevent loosening of the adjustable member 20 once it is inserted within eye 16.

FIG. 7 describes an additional element to the prior embodiments which externalizes in ears 76 and 78, formed or otherwise rigidly fixed to tongues 42 and 44. Surgical implements 80 and 82, visualized as elongated members having hooked end portions, engage ears 76 and 78 to separate or close tongues 42 and 44. Surgical implements may be employed during the initial insertion of intraocular lens 10 or post operatively where fluids change the shape of eye 16. In the latter case, a large incision of the eye is not necessary, since the implements may be pushed through the eye and removed after use without great disruption of the healing process.

The intraocular lens of the present invention may further comprise means 84 for continually forcing second tongue 44 away from first tongue 42 connected to lens portion 12. FIG. 8 illustrates an embodiment of forcing means 84 which includes a pair of studs 86 and 88 engaging a stretched elastomeric band 90. The force of band 90 may be predetermined to prevent the wedging action of first and second members 18 and 20 from damaging the angle 26 or any other portion of eye 16.

FIGS. 10 and 11 depict another embodiment of the present invention where adjustable member 20 takes a form of a projecting element 92 which extends away from the lens portion 12. Projecting element 92 fixes to lens portion 12 or is integrally formed therewith. Wedging piece 94 is slidably placed adjacent projecting element 92, FIGS. 10-13 illustrate wedging piece 94 as being on top of projecting element 92. Urging means 96 forces wedging piece 94 toward said projecting element 92. As shown in the drawings urging means may take the form of at least one elastic band 98 which surrounds a portion of projecting element. Two elastic bands 98 and 100 may also suffice for this purpose.

It should be noted that a gap 102 (partially defined by phantom lines of projecting element 92 in the Figures) is formed between leg 104 and supporting member 106. This permits the assembly of the adjustable member in that bands 100 and 102 easily slip into place. Leg 108 of member 92 angularly connects to leg 104.

FIGS. 12 and 13 shows another embodiment of the present invention where recesses 110, 112, 114, and 116 on wedging piece 94 encompass or partially surround a portion of bands 98 and 100. Likewise leg 104 of projecting element 92 may include recesses 118, 120, 122, and 124 which align with the recesses found on projecting element 92. Recesses 118, 120, 122, and 124 also encompass a portion of bands 98 and 100. The recesses prevent unwanted relative lateral movement between leg 104 of element 92 and wedging piece 94.

In operation, the surgeon selects an intraocular lens having the desired optical characteristics and inserts the same, through an incision, over the iris. Tongues 42 and 44 are adjusted such that the outer edge of tongue 44 wedges into angle 26 and the end portions of first member 18 wedge into angle 26. Where serrations are included, the surgeon selects the proper stop or position between the tongues. The eye is closed and examined during the post-operative period to insure the wedging of intraocular lens 10 does not dislocate. If the lens appears to be too loose or too tight, surgical implements are used to adjust the position of the tongues 42 and 44 without significant loss of aqueous humor; a brief and minor surgical procedure.

The embodiment shown in FIGS. 10–13, the surgeon merely places a lens which is slightly oversized in relation to interior of the eye. Wedging piece 94 is compressed slightly toward lens portion 12 and released such that urging means springs the lens 10 into place.

While in the foregoing specification embodiments of the invention have been set forth in considerable detail for purposes of making a complete disclosure of the invention, it will be apparent to those skilled in the art that numerous changes may be made in such details without departing from the spirit and principles of the invention.

What is claimed is:

1. An intraocular lens for an eye comprising:
   a. lens portion adapted for positioning over the pupil;
   b. first member adapted for extending away from said lens portion to the periphery of the iris and fixed to said lens;
   c. second adjustable member adapted for extending a selected distance away from said lens portion to the periphery of the iris and spaced along the periphery of the iris from said first member; said second adjustable member including a projecting element extending away from said lens portion and being fixed to said lens portion, a wedging piece having an edge portion adapted for extending to the periphery of the iris, and means for urging said wedging piece toward said projecting element.

2. The intraocular lens as claimed in claim 1 characterized in that said urging means includes at least one elastic band surrounding a portion of said projecting element and a portion of said wedging piece.

3. The intraocular lens as claimed in claim 2 characterized in that said projecting element includes a first leg having a second leg angularly connected thereto, and a supporting member, said wedging piece adapted for sliding contact with said second leg of said projecting element and said supporting member.

4. The intraocular lens as claimed in claim 3 characterized in that said second leg and said supporting member are in spaced relationship forming a gap therebetween.

5. The intraocular lens as claimed in claim 4 characterized in that said urging means includes two elastic bands spaced from one another and said second leg includes at least two recesses for encompassing a portion of each of said pair of elastic bands.

6. The intraocular lens as claimed in claim 5 characterized in that said second leg of said projecting element includes at least two recesses for encompassing a portion of each of said pair of elastic bands.

* * * * *